(12) United States Patent
Ishihara et al.

(10) Patent No.: US 7,655,442 B2
(45) Date of Patent: Feb. 2, 2010

(54) METHOD FOR STABILIZING MACROLIDE COMPOUNDS

(75) Inventors: Hiroshi Ishihara, Ibaraki (JP); Susumu Takeda, Kumamoto (JP); Tomonari Yamada, Shizuoka (JP); Yoshiaki Asahi, Shizuoka (JP)

(73) Assignees: Eisai R&D Management Co., Ltd., Tokyo (JP); Mercian Corporation, Tokyo (JP)

(*) Notice: Subject to any disclaimer, the term of this patent is extended or adjusted under 35 U.S.C. 154(b) by 534 days.

(21) Appl. No.: 10/587,042

(22) PCT Filed: Jan. 28, 2005

(86) PCT No.: PCT/JP2005/001637

§ 371 (c)(1),
(2), (4) Date: Jul. 24, 2006

(87) PCT Pub. No.: WO2005/073223

PCT Pub. Date: Aug. 11, 2005

(65) Prior Publication Data

US 2007/0155696 A1    Jul. 5, 2007

(30) Foreign Application Priority Data

Jan. 29, 2004  (JP) ............................. 2004-020804

(51) Int. Cl.
*C12P 19/62* (2006.01)
(52) U.S. Cl. ......................................... 435/76; 536/7.1
(58) Field of Classification Search .................. 536/7.1; 435/826
See application file for complete search history.

(56) References Cited

U.S. PATENT DOCUMENTS

| 4,480,033 A | 10/1984 | Suzuki et al. | |
|---|---|---|---|
| 5,472,954 A * | 12/1995 | Loftsson ....................... | 514/58 |

FOREIGN PATENT DOCUMENTS

| EP | 0147851 A2 | 7/1985 |
|---|---|---|
| EP | 1 380 579 A1 | 1/2004 |
| GB | 2006193 A | 5/1979 |
| JP | 58-177949 A | 10/1983 |
| JP | 58-179496 A | 10/1983 |
| JP | 4-352783 A | 12/1992 |
| JP | 9-48737 A | 2/1997 |
| JP | 11-509223 A | 8/1999 |
| JP | 2002-502810 A | 1/2002 |
| WO | WO-89/10739 A1 | 11/1989 |
| WO | WO-97/03654 A2 | 2/1997 |
| WO | WO-99/39694 A2 | 8/1999 |
| WO | WO-02/060890 A1 | 8/2002 |
| WO | WO-03/082845 A1 | 10/2003 |

OTHER PUBLICATIONS

Koontz et al., J. Agric. Food Chem., vol. 51, No. 24, pp. 7111-7114, Oct. 15, 2003.

* cited by examiner

*Primary Examiner*—Elli Peselev
(74) *Attorney, Agent, or Firm*—Birch, Stewart, Kolasch & Birch, LLP (57) ABSTRACT

The present invention provides a method for stabilizing a macrolide compound, and an efficient method for producing the compound. Specifically, it provides a method for stabilizing a macrolide compound, in which a 12-membered ring macrolide compound, such as a compound expressed by the formula (1) and a cyclodextrin are both present, and a method for producing a macrolide compound, in which a cyclodextrin is made to be present in a culture broth of actinomycetes having an ability of producing the macrolide compound.

11 Claims, 1 Drawing Sheet

Fig. 1

METHOD FOR STABILIZING MACROLIDE COMPOUNDS

TECHNICAL FIELD

The present invention relates to a method for stabilizing 12-membered ring macrolide compounds having an antitumor activity, and to a method for producing the compounds.

PRIOR ART

A 12-membered ring macrolide compound expressed by the formula (1):

11107B

(hereinafter referred to as macrolide compound 11107B) is an antitumor compound discovered in a cultured product of a *Streptomyces* sp. Mer-11107 strain, and furthermore chemical synthesis using this compound and analogs thereof as the raw material has been found to yield a macrolide compound having even better antitumor activity (see WO02/060890). However, these macrolide compounds are not sufficiently stable, particularly in an aqueous solution, and there has been a need for some way to improve their stability and produce them more efficiently.

Meanwhile, cyclodextrins are non-reducing sugars in which a glucose molecule is bonded in a ring by α-1,4 bonds, and α-, β- and γ-cyclodextrin, in which there are six, seven and eight glucose residues, respectively, are commonly known. Cyclodextrins have the property of forming complex with other compounds in their central cavity, and are used for stabilizing or solubilizing the included compound, preventing its oxidation, rendering it nonvolatile, and so forth. Also, cyclodextrins are known to have the effect of improving productivity when added to a culture medium in the fermentation of lankacidin antibiotics (see JP-A 58-177949 and JP-A 58-179496). However, cyclodextrins will not include just any compound, and even if they include a compound, they will not necessarily contribute to stabilization and so forth. Similarly, they do not improve productivity in the fermentation of just any compound.

DISCLOSURE OF THE INVENTION

It is an object of the present invention to provide a method for stabilizing macrolide compounds, and a method for efficiently producing the compounds.

The present invention relates to a method for stabilizing macrolide compounds (hereinafter referred to as macrolide compound (1)) expressed by the formula (1), wherein a macrolide compound (1) and a cyclodextrin are both made to be present:

(in the formula (1),
n is an integer from 0 to 4;
W is

$R^2, R^{3a}, R^{3b}, R^4, R^{5a}, R^{5b}, R^{6a}, R^{6b}, R^{7a}, R^{7b}, R^8, R^{9a}, R^{9b}, R^{10}, R^{16a}, R^{16b}, R^{17a}, R^{17b}, R^{na}$ and $R^{nb}$ are the same as or different from each other and each represents
(1) a hydrogen atom,
(2) a hydroxyl group,
(3)
   a) a $C_{1-22}$ alkyl group,
   b) a $C_{1-22}$ alkoxyl group,
   c) ArCH$_2$O— (in which Ar is a $C_{6-14}$ aryl group or a 5-membered to 14-membered heteroaryl group, each of which may have a substituent),
   d) a formyloxy group,
   e) a $C_{2-22}$ acyloxy group,
   f) an unsaturated $C_{3-23}$ acyloxy group,
   g) $R^{CO}$COO— (where $R^{CO}$ is a $C_{6-14}$ aryl group, a 5-membered to 14-membered heteroaryl group, a $C_{1-22}$ alkoxyl group, an unsaturated $C_{2-22}$ alkoxyl group, a $C_{6-14}$ aryloxy group or a 5-membered to 14-membered heteroaryloxy group, each of which may have a substituent),
   h) a $C_{1-22}$ alkylsulfonyloxy group,
   i) a $C_{6-14}$ arylsulfonyloxy group or
   j) $R^{s1}R^{s2}R^{s3}$Sio— (where $R^{s1}$, $R^{s2}$ and $R^{s3}$ are the same as or different from each other and are each represents a $C_{1-6}$ alkyl group or a $C_{6-14}$ aryl group), each of which may have a substituent,
(4) a halogen atom or
(5) $R^{N1}R^{N2}$N—$R^M$— (in which $R^M$ is a single bond or —CO—O—; $R^{N1}$ and $R^{N2}$ are
1) the same as or different from each other and each represents
   a) a hydrogen atom or
   b)
      (i) a $C_{1-22}$ alkyl group,
      (ii) an unsaturated $C_{2-22}$ alkyl group,
      (iii) a $C_{2-22}$ acyl group,
      (iv) an unsaturated $C_{3-23}$ acyl group,
      (v) a $C_{6-14}$ aryl group,
      (vi) a 5-membered to 14-membered heteroaryl group,
      (vii) a $C_{7-15}$ aralkyl group,
      (viii) a $C_{1-22}$ alkylsulfonyl group or
      (ix) a $C_{6-14}$ arylsulfonyl group, each of which may have a substituent, or 2) $R^{N1}$ and $R^{N2}$, together with the nitrogen atom to which they bound, represents a 3-membered to 14-membered nitrogen-containing non-aromatic heterocyclic group which may have a substituent); and $R^{12}$ and $R^{14}$ are the same as or different from each other and each represents a hydrogen atom or a $C_{1-6}$ alkyl group which may have a substituent, provided that

1) $R^2$, together with either $R^{3a}$ or $R^{3b}$, may form a partial structure:

2) $R^{3a}$ and $R^{3b}$, together with the carbon atom to which they bound, may form a ketone structure (=O) or an oxime structure {=NOR$^{OX}$ (in which R$^{OX}$ represents a $C_{1-22}$ alkyl group, an unsaturated $C_{2-22}$ alkyl group, a $C_{6-14}$ aryl group, a 5-membered to 14-membered heteroaryl group or a $C_{7-15}$ aralkyl group, each of which may have a substituent)}, 3) either $R^3a$ or $R^3b$ and either $R^6a$ or $R^6b$ may bound with an oxygen atom via the carbon atom to which they bound to form a partial structure:

4) $R^4$, together with either $R^{5a}$ or $R^{5b}$, may form a partial structure:

5) $R^{5a}$ and $R^{5b}$, together with the carbon atom to which they bound, may form a ketone structure (=O) or an oxime structure {=NOR$^{OX}$ (in which R$^{OX}$ has the same meaning as above)}, 6) $R^{6a}$ and $R^{6b}$, together with the carbon atom to which they bound, may form a spirooxirane ring or an exomethylene group, 7) either $R^{6a}$ or $R^{6b}$ and either $R^{7a}$ or $R^{7b}$, together with the carbon atom to which they bound, may form a 1,3-dioxolane ring, 8) $R^{7a}$ and $R^{7b}$, together with the carbon atom to which they bound, may form a ketone structure (=O) or an oxime structure {=NOR$^{OX}$ (in which R$^{OX}$ has the same meaning as above)}, 9) $R^8$, together with either $R^{9a}$ or $R^{9b}$, may form a partial structure:

10) $R^{9a}$ and $R^{9b}$, together with the carbon atom to which they bound, may form a ketone structure (=O) or an oxime structure {=NOR$^{OX}$ (in which R$^{OX}$ has the same meaning as above)}, and 11) $R^{na}$ and $R^{nb}$, together with the carbon atom to which they bound, may form a ketone structure (=O) or an oxime structure {=NOR$^{OX}$ (in which R$^{OX}$ has the same meaning as above)}).

The present invention also relates to a method for producing a macrolide compound selected from the group consisting of (8E,12E,14E)-3,6,7,21-tetrahydroxy-6,10,12,16,20-pentamethyl-18,19-epoxytricosa-8,12,14-trien-11-olide; (8E,12E,14E)-7-acetoxy-3,6,21-trihydroxy-6,10,12,16,20-pentamethyl-18,19-epoxytricosa-8,12,14-trien-11-olide; (8E,12E,14E)-7-acetoxy-3,6-dihydroxy-6,10,12,16,20-pentamethyl-21-oxo-18,19-epoxytricosa-8,12,14-trien-11-olide; (8E,12E,14E)-7-acetoxy-3,6,16,21-tetrahydroxy-6,10,12,16,20-pentamethyl-18,19-epoxytricosa-8,12,14-trien-11-olide; (8E,12E,14E)-7-acetoxy-3,6,20,21-tetrahydroxy-6,10,12,16,20-pentamethyl-18,19-epoxytricosa-8,12,14-trien-11-olide; (8E,12E,14E)-3,6,7,16,21-pentahydroxy-6,10,12,16,20-pentamethyl-18,19-epoxytricosa-8,12,14-trien-11-olide; (8E,12E,14E)-3,6,7,20,21-pentahydroxy-6,10,12,16,20-pentamethyl-18,19-epoxytricosa-8,12,14-trien-11-olide; (4E,8E,12E,14E)-7-acetoxy-3,6,21-trihydroxy-6,10,12,16,20-pentamethyl-18,19-epoxytricosa-4,8,12,14-tetraen-11-olide; (8E,12E,14E)-3,6,21-trihydroxy-6,10,12,16,20-pentamethyl-7-propanoyloxy-18,19-epoxytricosa-8,12,14-trien-11-olide; (8E,12E,14E)-7-acetoxy-3,6,21-trihydroxy-6,10,12,16,20-pentamethyl-18,19-epoxydocosa-8,12,14-trien-11-olide; (8E,12E,14E)-7-acetoxy-3,5,6,21-tetrahydroxy-6,10,12,16,20-pentamethyl-18,19-epoxytricosa-8,12,14-trien-11-olide; (8E,12E,14E)-5,7-diacetoxy-3,6,21-trihydroxy-6,10,12,16,20-pentamethyl-18,19-epoxytricosa-8,12,14-trien-11-olide; (8E,12E,14E)-3,7-diacetoxy-6,21-dihydroxy-6,10,12,16,20-pentamethyl-18,19-epoxytricosa-8,12,14-trien-11-olide; (8E,12E,14E)-7-acetoxy-6-acetoxymethyl-3,6,21-trihydroxy-10,12,16,20-tetramethyl-18,19-epoxytricosa-8,12,14-trien-11-olide; (8E,12E,14E)-7-acetoxy-3,6,17,21-tetrahydroxy-6,10,12,16,20-pentamethyl-18,19-epoxytricosa-8,12,14-trien-11-olide; (8E,12E,14E)-7-acetoxy-3,6,20-trihydroxy-6,10,12,16-tetramethyl-18,19-epoxyheneicosa-8,12,14-trien-11-olide; (4E,8E,12E,14E)-3,6,7,21-tetrahydroxy-6,10,12,16,20-pentamethyl-18,19-epoxytricosa-4,8,12,14-tetraen-11-olide; (8E,12E,14E)-7-acetoxy-3,6,21-trihydroxy-6,10,12,16-tetramethyl-18,19-epoxytricosa-8,12,14-trien-11-olide; (8E,12E,14E)-7-acetoxy-3,6,21-trihydroxy-6,10,12,20-tetramethyl-18,19-epoxytricosa-8,12,14-trien-11-olide; (12E,14E)-3,6,21-trihydroxy-6,10,12,16,20-pentamethyl-9-oxo-18,19-epoxytricosa-12,14-dien-11-olide; (8E,12E,14E)-7-acetoxy-3,6,21-trihydroxy-6,10,16,20-tetramethyl-18,19-epoxytricosa-8,12,14-trien-11-olide; (8E,12E,14E)-7-acetoxy-3,6,21-trihydroxy-2,6,10,12,16,20-hexamethyl-18,19-epoxytricosa-8,12,14-trien-11-olide; (8E,12E,14E)-7-acetoxy-3,5,21-trihydroxy-6,10,12,16,20-pentamethyl-18, 19-epoxytricosa-8,12,14-trien-11-olide; (8E,12E,14E)-7-acetoxy-3,6,21-trihydroxy-6,12,16,20-tetramethyl-18,19-epoxytricosa-8,12,14-trien-11-olide; (8E,12E,14E)-6-acetoxymethyl-3,6,7,21-tetrahydroxy-10,12,16,20-tetramethyl-18,19-epoxytricosa-8,12,14-trien-11-olide; (8E,12E,14E)-3,6,7-trihydroxy-6,10,12,16,20-pentamethyl-21-oxo-18,19-epoxytricosa-8,12,14-trien-11-olide; a 3-position isomer of (8E,12E,14E)-7-acetoxy-3,6,21-trihydroxy-6,10,12,16,20-pentamethyl-18,19-epoxytricosa-8,12,14-trien-11-olide; (8E,12E,14E)-7-acetoxy-3,6,21-trihydroxy-10,12,16,20-tetramethyl-18,19-epoxytricosa-8,12,14-trien-11-olide; (8E,12E,14E)-6-acetoxy-3,7,21-trihydroxy-10,12,16,20-tetramethyl-18,19-epoxytricosa-8,12,14-trien-11-olide; (8E,12E,14E)-3,6,7,21-tetrahydroxy-2,6,10,12,16,20-hexamethyl-18,19-epoxytricosa-8,12,14-trien-11-olide; (8E,12E,14E,18E)-7-acetoxy-3,6,21,22-tetrahydroxy-6,10,12,16,20-pentamethyltricosa-8,12,14,18-tetraen-11-olide; (8E,12E,14E)-3,7,21-trihydroxy-10,12,16,20-tetramethyl-18,19-epoxytricosa-8,12,14-trien-11-olide; (4E,8E,12E,14E)-7-acetoxy-3,6-dihydroxy-6,10,12,16,20-pentamethyl-21-oxo-18,19-epoxytricosa-4,8,12,14-tetraen-11-olide; (8E,12E,14E)-7-acetoxy-3,21-dihydroxy-10,12,16,20-tetramethyl-18,19-epoxy-6,6-(epoxymethano)tricosa-8,12,14-trien-11-olide; (4E,8E,12E,14E)-7-acetoxy-3,21-dihydroxy-10,12,16,20-tetramethyl-18,19-epoxy-6,6-(epoxymethano)tricosa-4,8,12,14-tetraen-11-olide; (8E,12E,14E)-3,7,21-trihydroxy-10,12,16,20-tetramethyl-18,19-epoxy-6,6-(epoxymethano)tricosa-8,12,14-trien-11-olide; (4E,8E,12E,14E)-6,7-diacetoxy-3,21-dihydroxy-6,10,12,16,20-pentamethyl-18,19-epoxytricosa-4,8,12,14-tetraen-11-olide; (8E,12E,14E)-6,7-diacetoxy-3,21-dihydroxy-6,10,12,16,20-pentamethyl-18,19-epoxytricosa-8,12,14-trien-11-olide; (8E,12E,14E)-7-acetoxy-3,6,16-trihydroxy-6,10,12,16,20-pentamethyl-21-oxo-18,19-epoxytricosa-8,12,14-trien-11-olide; (8E,12E,14E)-7-acetoxy-3,6,21,22-tetrahydroxy-6,10,12,16,20-pentamethyl-18,19-epoxytricosa-8,12,14-trien-11-olide; (4E,8E,12E,14E)-7-acetoxy-3,6,17,21-tetrahydroxy-6,10,12,16,20-pentamethyl-18,19-epoxytricosa-4,8,12,14-tetraen-11-olide; (8E,12E,14E)-7-acetoxy-3,6,17-trihydroxy-6,10,12,16-tetramethyl-18,19-epoxyheneicosa-8,12,14-trien-11-olide; (8E,12E,14E)-7-acetoxy-3,5,6,21,22-pentahydroxy-6,10,12,16,20-pentamethyl-18,19-epoxytricosa-8,12,14-trien-11-olide; (8E,12E,14E)-7-acetoxy-3,6,16-trihydroxy-6,10,12,16-tetramethyl-18,19-epoxyheneicosa-8,12,14-trien-11-olide; (8E,12E,14E)-3,6,7,21-tetrahydroxy-6,10,16,20-tetramethyl-18,19-epoxytricosa-8,12,14-trien-11-olide; (8E,12E,14E)-7-acetoxy-3,6,17,21-tetrahydroxy-6,10,12,16,20-pentamethyl-18,19-epoxytricosa-8,12,14-trien-11-olide; (8E,12E,14E)-7-acetoxy-3,6,17-trihydroxy-6,10,12,16,18-pentamethyl-18,19-epoxyheneicosa-8,12,14-trien-11-olide; (8E,12E,14E)-7-acetoxy-3,6,21-trihydroxy-6,10,12,16,20-pentamethyl-5-oxo-18,19-epoxytricosa-8,12,14-trien-11-olide; and (8E,12E,14E,18E)-7-acetoxy-3,6,21-trihydroxy-6,10,12,16,20-pentamethyltricosa-8,12,14,18-tetraen-11-olide (hereinafter referred to as macrolide compound (2) group), wherein cyclodextrins are made to be present in a culture broth of actinomycetes having an ability of producing the macrolide compounds.

DETAILED DESCRIPTION OF THE INVENTION

Method for Stabilizing Macrolide Compounds

In the stabilization method of the present invention, it is necessary for the macrolide compound (1) and cyclodextrins both to be present. Cyclodextrins may be made to be present in a solid phase or a solution, and particularly a solution, and preferably a water-containing solution, that contains the macrolide compound (1).

Conventional preparation carriers can be used for the solid phase containing a macrolide compound, and these can be produced by a conventional method. Specifically, when a solid preparation for oral use is prepared, a filler is added to the macrolide compound (1), and if necessary, a binder, disintegrant, lubricant, colorant, flavoring, and the like are also added, then the composition is made into tablets, coated tablets, granules, a powder, capsules, or the like. Naturally, a sugar coating, gelatin coating, or any other suitable coating may given to the tablets or granules as needed.

In the present invention, anticancer drugs that are effective for solid cancers and the like have been found in the products of fermenting strains of the genus *Streptomyces* and variants thereof, and in derivatives of these fermentation products.

In addition to aqueous solutions, examples of solutions of the macrolide compound (1) include water-containing solutions that contain not more than 50 vol % an organic solvent that is miscible with water (such as methanol, ethanol, 1-propanol, 2-propanol, acetone or acetonitrile), but an aqueous solution is preferable. There are no particular restrictions on the concentration of the macrolide compound (1) in the solution, but from 0.001 to 5 wt % is preferable and from 0.005 to 0.5 wt % is even better.

The amount of cyclodextrin used when a cyclodextrin is made to be present is preferably from 0.1 to 1000 parts (by molar ratio) and even more preferably 1 to 100 parts, with respect to the macrolide compound (1).

Examples of the macrolide compound (1) used in the stabilization method of the present invention include macrolide compounds expressed by the formulae (1-1) and (1-2).

(1-1)

In the formula (1-1), n, $R^2$, $R^{3a}$, $R^{3b}$, $R^4$, $R^{5a}$, $R^{5b}$, $R^{6a}$, $R^{6b}$, $R^{7a}$, $R^{7b}$, $R^8$, $R^{9a}$, $R^{9b}$, $R^{10}$, $R^{12}$, $R^{14}$, $R^{16a}$, $R^{16b}$, $R^{17a}$, $R^{17b}$, $R^{na}$ and $R^{nb}$ have the same meanings as those defined in the formula (1).

(1-2)

In the formula (1-2), n, $R^2$, $R^{3a}$, $R^{3b}$, $R^4$, $R^{5a}$, $R^{5b}$, $R^{6a}$, $R^{6b}$, $R^{7a}$, $R^{7b}$, $R^8$, $R^{9a}$, $R^{9b}$, $R^{10}$, $R^{12}$, $R^{14}$, $R^{16a}$, $R^{16b}$, $R^{17a}$, $R^{17b}$, $R^{na}$ and $R^{nb}$ have the same meanings as those defined in the formula (1).

The "halogen atom" used in the specification of the present application means a fluorine atom, a chlorine atom, a bromine atom and an iodine atom.

The "$C_{1-22}$ alkyl group" used in the specification of the present application indicates a linear or branched alkyl group having 1 to 22 carbon atoms, such as methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, n-hexyl group, 1-ethyl-2-methylpropyl group, 1,1,2-trimethylpropyl group, 1-ethylbutyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group, n-heptyl group, n-octyl group, n-nonyl group or n-decyl group; preferably a linear or branched alkyl group having 1 to 6 carbon atoms (a $C_{1-6}$ alkyl group), such as methyl group, ethyl group, n-propyl group, iso-propyl group, n-butyl group, iso-butyl group, sec-butyl group or tert-butyl group.

The "unsaturated $C_{2-22}$ alkyl group" used in the specification of the present application indicates a linear or branched alkenyl group having 2 to 22 carbon atoms or a linear or branched alkynyl group having 2 to 22 carbon atoms, such as vinyl group, allyl group, 1-propenyl group, isopropenyl group, 2-methyl-1-propenyl group, 2-methyl-2-propenyl group, 1-butenyl group, 2-butenyl group, 3-butenyl group, 1-pentenyl group, 1-hexenyl group, 1,3-hexadienyl group, 1,6-hexadienyl group, ethynyl group, 1-propynyl group, 2-propynyl group, 1-butynyl group, 2-butynyl group, 3-butynyl group, 1-ethynyl-2-propynyl group, 2-methyl-3-propynyl group, 1-pentynyl group, 1-hexynyl group, 1,3-hexadiynyl group or 1,6-hexadiynyl group. It preferably indicates a linear or branched alkenyl group having 2 to 10 carbon atoms or a linear or branched alkynyl group having 2 to 10 carbon atoms, such as vinyl group, allyl group, 1-propenyl group, isopropenyl group, ethynyl group, 1-propynyl group, 2-propynyl group, 1-butynyl group, 2-butynyl group or 3-butynyl group.

The "$C_{6-14}$ aryl group" used in the specification of the present application means an aromatic hydrocarbon group having 6 to 14 carbon atoms, and a monocyclic group and condensed rings such as a bicyclic group and a tricyclic group are included. Examples thereof are phenyl group, indenyl group, 1-naphthyl group, 2-naphthyl group, azulenyl group, heptalenyl group, indacenyl group, acenaphthyl group, fluorenyl group, phenalenyl group, phenanthrenyl group and anthracenyl group; of which a preferred example is phenyl group, 1-naphthyl group or 2-naphthyl group.

The "5-membered to 14-membered heteroaryl group" used in the specification of the present application means a monocyclic, bicyclic or tricyclic 5-membered to 14-membered aromatic heterocyclic group which contains one or more of hetero atoms selected from the group consisting of a nitrogen atom, sulfur atom and oxygen atom. Preferred examples thereof are a nitrogen-containing aromatic heterocyclic group such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizinyl group, phthalazinyl group, naphthyridinyl group, quinoxalinyl group, quinazolinyl group, cinnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenazinyl group, imidazopyridyl group, imidazopyrimidinyl group or pyrazolopyridyl group; a sulfur-containing aromatic heterocyclic group such as thienyl group or benzothienyl group; and an oxygen-containing aromatic heterocyclic group such as furyl group, pyranyl group, cyclopentapyranyl group, benzofuranyl group or isobenzofuranyl group; an aromatic heterocyclic group containing two or more different hetero atoms, such as thiazolyl group, isothiazolyl group, benzothiazolyl group, benzothiadiazolyl group, phenothiazinyl group, isoxazolyl group, furazanyl group, phenoxazinyl group, oxazolyl group, isoxazoyl group, benzoxazolyl group, oxadiazolyl group, pyrazolooxazolyl group, imidazothiazolyl group, thienofuranyl group, furopyrrolyl group or pyridoxazinyl group, of which a preferred example is thienyl group, furyl group, pyridyl group, pyridazinyl group, pyrimidinyl group or pyrazinyl group.

The "3-membered to 14-membered nitrogen-containing non-aromatic heterocyclic group" used in the specification of the present application means a monocyclic, bicyclic or tricyclic 3-membered to 14-membered non-aromatic heterocyclic group containing one or more nitrogen atoms. Preferable examples thereof include an azilidinyl group, azetizinyl group, pyrrolidinyl group, pyrrolyl group, piperidyl group, piperazinyl group, homopiperidinyl group, homopiperazinyl group, imidazolyl group, pyrazolidinyl group, imidazolidinyl, morpholinyl group, imidazolinyl group, oxazolinyl group and quinuclidinyl group. The nitrogen-containing non-aromatic heterocyclic group also includes a group derived from a pyridone ring and a non-aromatic condensed ring (such as a group derived from a phthalimide ring or succinimide ring).

The "$C_{2-22}$ acyl group" used in the specification of the present application means a group in which a terminal in the above-defined "$C_{1-22}$ alkyl group" is a carbonyl group. Examples include an acetyl group, propionyl group, butyryl group, iso-butyryl group, valeryl group, iso-valeryl group, pivaloyl group, caproyl group, decanoyl group, lauroyl group, myristoyl group, palmitoyl group, stearoyl group and arachidoyl group. An acyl group having 2 to 6 carbon atoms such as an acetyl group, propionyl group, butyryl group or iso-butyryl group is preferable.

The "unsaturated $C_{3-23}$ acyl group" used in the specification of the present application means a group corresponding to the above-defined "unsaturated $C_{2-22}$ alkyl group" to which end a carboxyl group is bonded. Examples thereof are an acryloyl group, propioloyl group, crotonoyl group, iso-crotonoyl group, oleoyl group, and linolenoyl group. An unsaturated acyl group having 3 to 6 carbon atoms such as an acryloyl group is preferable.

The "$C_{2-22}$ acyloxy group" used in the specification of the present application means a group corresponding to the above-defined "$C_{1-22}$ acyl group" to which end an oxygen atom is bonded. Suitable examples thereof are an acetoxy group, propionyloxy group, butyryloxy group, iso-butyryloxy group, valeryloxy group, iso-valeryloxy group, pivaloyloxy group, caproyloxy group, decanoyloxy group, lauroyloxy group, myristoyloxy group, palmitoyloxy group, stearoyloxy group and arachidoyloxy group. An acyloxy group having 2 to 6 carbon atoms such as an acetoxy group, propionyloxy group, butyryloxy group or iso-butyryloxy group is preferable.

The "unsaturated $C_{3-23}$ acyloxy group" used in the specification of the present application means a group corresponding to the above-defined "unsaturated $C_{3-23}$ acyl group" to which end an oxygen atom is bonded. Suitable examples thereof are an acryloyloxy group, propioloyloxy group, crotonoyloxy group, iso-crotonoyloxy group, oleoyloxygroup and linolenoyloxy group. An unsaturated acyloxy group having 3 to 6 carbon atoms such as an acryloyloxy group is preferable.

The "$C_{7-15}$ aralkyl group" used in the specification of the present application means a group having 7 to 15 carbon atoms and corresponding to the above-defined "$C_{1-22}$ alkyl group" in which the substitutable site is substituted with the above-mentioned "$C_{6-14}$ aryl group". Specific examples include a benzyl group, phenethyl group, 3-phenylpropyl group, 4-phenylbutyl group, 1-naphthylmethyl group, and 2-naphthylmethyl group. An aralkyl group having 7 to 10 carbon atoms such as a benzyl group or phenethyl group is preferable.

The "$C_{1-22}$ alkoxy group" used in the specification of the present application means a group corresponding to the above-defined "$C_{1-22}$ alkyl group" to which end an oxygen atom is bonded. Suitable examples thereof are methoxy group, ethoxy group, n-propoxy group, iso-propoxy group, n-butoxy group, iso-butoxy group, sec-butoxy group, tert-butoxy group, n-pentyloxy group, iso-pentyloxy group, sec-pentyloxy group, n-hexyloxy group, iso-hexyloxy group, 1,1-dimethylpropoxy group, 1,2-dimethylpropoxy group, 2,2-dimethylpropoxy group, 2-ethylpropoxy group, 1-ethyl-2-methylpropoxy group, 1,1,2-trimethylpropoxy group, 1,1,2-trimethylpropoxy group, 1,1-dimethylbutoxy group, 1,2-dimethylbutoxy group, 2,2-dimethylbutoxy group, 2,3-dimethylbutyloxy group, 1,3-dimethylbutyloxy group, 2-ethylbutoxy group, 2-methylpentoxy group and 3-methylpentoxy group.

The "unsaturated $C_{2-22}$ alkoxy group" used in the specification of the present application means a group corresponding to the above-defined "unsaturated $C_{2-22}$ alkyl group" to which end an oxygen atom is bonded. Preferable examples include a vinyloxy group, allyloxy group, 1-propenyloxy group, isopropenyloxy group, 2-methyl-1-propenyloxy group, 2-methyl-2-propenyloxy group, 1-butenyloxy group, 2-butenyloxy group, 3-butenyloxy group, 1-pentenyloxy group, 1-hexenyloxy group, 1,3-hexadienyloxy group, 1,6-hexadienyloxy group, propargyloxy group and 2-butynyloxy group.

The "$C_{6-14}$ aryloxy group" used in the specification of the present application means a group corresponding to the above-defined "$C_{6-14}$ aryl group" to which end an oxygen atom is bonded. Specific examples include a phenoxy group, indenyloxy group, 1-naphthyloxy group, 2-naphthyloxy group, azulenyloxy group, heptalenyloxy group, indacenyloxy group, acenaphthyloxy group, fluorenyloxy group, phenalenyloxy group, phenanthrenyloxy group and anthracenyloxy group.

The "5-membered to 14-membered heteroaryloxy group" used in the specification of the present application means a group corresponding to the above-defined "5-membered to 14-membered heteroaryl group" to which end an oxygen atom is bonded. Specific examples include a pyrrolyloxy group, pyridyloxy group, pyridazinyloxy group, pyrimidinyloxy group, pyrazinyloxy group, triazolyloxy group, tetrazolyloxy group, benzotriazolyloxy group, pyrazolyloxy group, imidazolyloxy group, benzimidazolyloxy group, indolyloxy group, isoindolyloxy group, indolizinyloxy group, purinyloxy group, indazolyloxy group, quinolyloxy group, isoquinolyloxy group, quinolizinyloxy group, phthalazinyloxy group, naphthyridinyloxy group, quinoxalyloxy group, quinazolinyloxy group, cinnolinyloxy group, pteridinyloxy group, imidazotriazinyloxy group, pyrazinopyridazinyloxy group, acridinyloxy group, phenanthridinyloxy group, carbazolyloxy group, carbazolinyloxy group, perimidinyloxy group, phenanthrolinyloxy group, phenazinyloxy group, imidazopyridyloxy group, imidazopyrimidinyloxy group, pyrazolopyridyloxy group, thienyloxy group, benzothienyloxy group, furyloxy group, pyranyloxy group, cyclopentapyranyloxy group, benzofuryloxy group, isobenzofuryloxy group, thiazolyloxy group, isothiazolyloxy group, benzothiazolyloxy group, benzthiadiazolyloxy group, phenothiazinyloxy group, isoxazolyloxy group, furazanyloxy group, phenoxazinyloxy group, oxazolyloxy group, isoxazolyloxy group, benzoxazolyloxy group, oxadiazolyloxy group, pyrazolooxazolyloxy group, imidazothiazolyloxy group, thienofuranyloxy group, furopyrrolyloxy group and pyridoxazinyloxy group. A thienyloxy group, furyloxy group, pyridyloxy group, pyridazinyloxy group, pyrimidinyloxy group and pyrazinyloxy group are preferred.

The "$C_{1-22}$ alkylsulfonyl group" used in the specification of the present application means a sulfonyl group to which the above-defined "$C_{1-22}$ alkyl group" is bound. Specific examples thereof are methylsulfonyl group, ethylsulfonyl group, n-propylsulfonyl group and iso-propylsulfonyl group.

The "$C_{6-14}$ arylsulfonyl group" used in the specification of the present application means a sulfonyl group to which the above-defined "$C_{6-14}$ aryl group" is bound. Specific examples thereof are benzenesulfonyl group, 1-naphthalenesulfonyl group and 2-naphthalenesulfonyl group.

The "$C_{1-22}$ alkylsulfonyloxy group" used in the specification of the present application means a group corresponding to the above-defined "$C_{1-22}$ alkylsulfonyl group" to which end an oxygen atom is bonded. Examples thereof are methylsulfonyloxy group, ethylsulfonyloxy group, n-propylsulfonyloxy group and iso-propylsulfonyloxy group.

The "$C_{6-14}$ arylsulfonyloxy group" used in the specification of the present application means a group corresponding to the above-defined "$C_{6-14}$ arylsulfonyl group" to which end an oxygen atom is bonded. Examples thereof are benzenesulfonyloxy group, 1-naphthalenesulfonyloxy group and 2-naphthalenesulfonyloxy group.

Examples of the substituent in the term "may have a substituent" used in the specification of the present application include those selected from the group consisting of:

(1) a halogen atom;

(2) a hydroxyl group;

(3) a thiol group;

(4) a nitro group;

(5) a nitroso group;

(6) a cyano group;

(7) a carboxyl group;

(8) a hydroxysulfonyl group;

(9) an amino group;

(10) a $C_{1-22}$ alkyl group (for example, methyl group, ethyl group, n-propyl group, iso-propyl group, n-butyl group, iso-butyl group, sec-butyl group and tert-butyl group);

(11) an unsaturated $C_{2-22}$ alkyl group (for example, vinyl group, allyl group, 1-propenyl group, isopropenyl group, ethynyl group, 1-propynyl group, 2-propynyl group, 1-butynyl group, 2-butynyl group and 3-butynyl group);

(12) a $C_{6-14}$ aryl group (for example, phenyl group, 1-naphthyl group and 2-naphthyl group);

(13) a 5-membered to 14-membered heteroaryl group (for example, thienyl group, furyl group, pyridyl group, pyridazinyl group, pyrimidinyl group and pyrazinyl group);

(14) a 3-membered to 14-membered nitrogen-containing non-aromatic heterocyclic group (for example, aziridinyl group, azetidinyl group, pyrrolidinyl group, pyrrolyl group, piperidyl group, piperazinyl group, imidazolyl group, pyrazolidinyl group, imidazolidinyl, morpholinyl group, imidazolinyl group, oxazolinyl group and quinuclidinyl group);

(15) a $C_{1-22}$ alkoxy group (for example, methoxy group, ethoxy group, n-propoxy group, iso-propoxy group, sec-propoxy group, n-butoxy group, iso-butoxy group, sec-butoxy group and tert-butoxy group);

(16) a $C_{6-14}$ aryloxy group (for example, phenoxy group, 1-naphthyloxy group and 2-naphthyloxy group);

(17) a $C_{7-22}$ aralkyloxy group (for example, benzyloxy group, phenethyloxy group, 3-phenylpropoxy group, 4-phenylbutyloxy group, 1-naphthylmethyloxy group and 2-naphthylmethyloxy group);

(18) a 5-membered to 14-membered heteroaryloxy group (for example, thienyloxy group, furyloxy group, pyridyloxy group, pyridazinyloxy group, pyrimidinyloxy group and pyrazinyloxy group);

(19) a $C_{2-23}$ acyl group (for example, acetyl group, propionyl group, butyryl group, iso-butyryl group, valeryl group, iso-valeryl group, pivaloyl group, caproyl group, decanoyl group, lauroyl group, myristoyl group, palmitoyl group, stearoyl group and arachidoyl group);

(20) a $C_{7-15}$ aroyl group (for example, benzoyl group, 1-naphthoyl group and 2-naphthoyl group);

(21) a $C_{3-23}$ unsaturated acyl group (for example, acryloyl group, propioloyl group, crotonoyl group, iso-crotonoyl group, oleoyl group and linolenoyl group), (22) a $C_{2-23}$ acyloxy group (for example, acetoxy group, propionyloxy group and pivalyloxy group), (23) a $C_{2-22}$ alkoxycarbonyl group (for example, methoxycarbonyl group, ethoxycarbonyl group, n-propoxycarbonyl group, iso-propoxycarbonyl group, n-butoxycarbonyl group, iso-butoxycarbonyl group, sec-butoxycarbonyl group and tert-butoxycarbonyl group);

(24) an unsaturated $C_{3-22}$ alkoxycarbonyl group (for example, vinyloxycarbonyl group, aryloxycarbonyl group, 1-propenyloxycarbonyl group, isopropenyloxycarbonyl group, propalgyloxycarbonyl group and 2-butynyloxycarbonyl group);

(25) a $C_{1-22}$ alkylsulfonyl group (for example, methylsulfonyl group, ethylsulfonyl group, n-propylsulfonyl group and iso-propylsulfonyl group);

(26) a $C_{6-14}$ arylsulfonyl group (for example, benzenesulfonyl group, 1-naphthalenesulfonyl group and 2-naphthalenesulfonyl group); and (27) a $C_{1-22}$ alkylsulfonyloxy group (for example, methylsulfonyloxy group, ethylsulfonyloxy group, n-propylsulfonyloxy group and iso-propylsulfonyloxy group).

Examples of the macrolide compound expressed by the formula (1-1) include (8E,12E,14E)-3,6,7,21-tetrahydroxy-6,10,12,16,20-pentamethyl-18,19-epoxytricosa-8,12,14-trien-11-olide; (8E,12E,14E)-7-acetoxy-3,6,21-trihydroxy-6,10,12,16,20-pentamethyl-18,19-epoxytricosa-8,12,14-trien-11-olide; (8E,12E,14E)-7-acetoxy-3,6-dihydroxy-6,10,12,16,20-pentamethyl-21-oxo-18,19-epoxytricosa-8,12,14-trien-11-olide; (8E,12E,14E)-7-acetoxy-3,6,16,21-tetrahydroxy-6,10,12,16,20-pentamethyl-18,19-epoxytricosa-8,12,14-trien-11-olide; (8E,12E,14E)-7-acetoxy-3,6,20,21-tetrahydroxy-6,10,12,16,20-pentamethyl-18,19-epoxytricosa-8,12,14-trien-11-olide; (8E,12E,14E)-3,6,7,16,21-pentahydroxy-6,10,12,16,20-pentamethyl-18,19-epoxytricosa-8,12,14-trien-11-olide; (8E,12E,14E)-3,6,7,20,21-pentahydroxy-6,10,12,16,20-pentamethyl-18,19-epoxytricosa-8,12,14-trien-11-olide; (4E,8E,12E,14E)-7-acetoxy-3,6,21-trihydroxy-6,10,12,16,20-pentamethyl-18,19-epoxytricosa-4,8,12,14-tetraen-11-olide; (8E,12E,14E)-3,6,21-trihydroxy-6,10,12,16,20-pentamethyl-7-propanoyloxy-18,19-epoxytricosa-8,12,14-trien-11-olide; (8E,12E,14E)-7-acetoxy-3,6,21-trihydroxy-6,10,12,16,20-pentamethyl-18,19-epoxydocosa-8,12,14-trien-11-olide; (8E,12E,14E)-7-acetoxy-3,5,6,21-tetrahydroxy-6,10,12,16,20-pentamethyl-18,19-epoxytricosa-8,12,14-trien-11-olide; (8E,12E,14E)-5,7-diacetoxy-3,6,21-trihydroxy-6,10,12,16,20-pentamethyl-18,19-epoxytricosa-8,12,14-trien-11-olide; (8E,12E,14E)-3,7-diacetoxy-6,21-dihydroxy-6,10,12,16,20-pentamethyl-18,19-epoxytricosa-8,12,14-trien-11-olide; (8E,12E,14E)-7-acetoxy-6-acetoxymethyl-3,6,21-trihydroxy-10,12,16,20-tetramethyl-18,19-epoxytricosa-8,12,14-trien-11-olide; (8E,12E,14E)-7-acetoxy-3,6,17,21-tetrahydroxy-6,10,12,16,20-pentamethyl-18,19-epoxytricosa-8,12,14-trien-11-olide; (8E,12E,14E)-7-acetoxy-3,6,20-trihydroxy-6,10,12,16-tetramethyl-18,19-epoxyheneicosa-8,12,14-trien-11-olide; (4E,8E,12E,14E)-3,6,7,21-tetrahydroxy-6,10,12,16,20-pentamethyl-18,19-epoxytricosa-4,8,12,14-tetraen-11-olide; (8E,12E,14E)-7-acetoxy-3,6,21-trihydroxy-6,10,12,16-tetramethyl-18,19-epoxytricosa-8,12,14-trien-11-olide; (8E,12E,14E)-7-acetoxy-3,6,21-trihydroxy-6,10,12,20-tetramethyl-18,19-epoxytricosa-8,12,14-trien-11-olide; (12E,14E)-3,6,21-trihydroxy-6,10,12,16,20-pentamethyl-9-oxo-18,19-epoxytricosa-12,14-dien-11-olide; (8E,12E,14E)-7-acetoxy-3,6,21-trihydroxy-6,10,16,20-tetramethyl-18,19-epoxytricosa-8,12,14-trien-11-olide; (8E,12E,14E)-7-acetoxy-3,6,21-trihydroxy-2,6,10,12,16,20-hexamethyl-18,19-epoxytricosa-8,12,14-trien-11-olide; (8E,12E,14E)-7-acetoxy-3,5,21-trihydroxy-6,10,12,16,20-pentamethyl-18,19-epoxytricosa-8,12,14-trien-11-olide; (8E,12E,14E)-7-acetoxy-3,6,21-trihydroxy-6,12,16,20-tetramethyl-18,19-epoxytricosa-8,12,14-trien-11-olide; (8E,12E,14E)-6-acetoxymethyl-3,6,7,21-tetrahydroxy-10,12,16,20-tetramethyl-18,19-epoxytricosa-8,12,14-trien-11-olide; (8E,12E,14E)-3,6,7-trihydroxy-6,10,12,16,20-pentamethyl-21-oxo-18,19-epoxytricosa-8,12,14-trien-11-olide; a 3-position isomer of (8E,12E,14E)-7-acetoxy-3,6,21-trihydroxy-6,10,12,16,20-pentamethyl-18,19-epoxytricosa-8,12,14-trien-11-olide; (8E,12E,14E)-7-acetoxy-3,6,21-trihydroxy-10,12,16,20-tetramethyl-18,19-epoxytricosa-8,12,14-trien-11-olide; (8E,12E,14E)-6-acetoxy-3,7,21-trihydroxy-10,12,16,20-tetramethyl-18,19-epoxytricosa-8,12,14-trien-11-olide; (8E,12E,14E)-3,6,7,21-tetrahydroxy-2,6,10,12,16,20-hexamethyl-18,19-epoxytricosa-8,12,14-trien-11-olide; (8E,12E,14E)-3,7,21-trihydroxy-10,12,16,20-tetramethyl-18,19-epoxytricosa-8,12,14-trien-11-olide; (4E,8E,12E,14E)-7-acetoxy-3,6-dihydroxy-6,10,12,16,20-pentamethyl-21-oxo-18,19-epoxytricosa-4,8,12,14-tetraen-11-olide; (8E,12E,14E)-7-acetoxy-3,21-dihydroxy-10,12,16,20-tetramethyl-18,19-epoxy-6,6-(epoxymethano)tricosa-8,12,14-trien-11-olide; (4E,8E,12E,14E)-7-acetoxy-3,21-dihydroxy-epoxytricosa-8,12,14-trien-11-olide; (8E,12E,14E)-7-acetoxy-3,6,21-trihydroxy-2,6,10,12,16,20-hexamethyl-18,19-epoxytricosa-8,12,14-trien-11-olide; (8E,12E,14E)-7-acetoxy-3,5,21-trihydroxy-6,10,12,16,20-pentamethyl-18, 19-epoxytricosa-8,12,14-trien-11-olide; (8E,12E,14E)-7-acetoxy-3,7,21-trihydroxy-6,12,16,20-tetramethyl-18,19-epoxytricosa-8,12,14-trien-11-olide; (8E,12E,14E)-6-acetoxymethyl-3,6,7,21-tetrahydroxy-10,12,16,20-tetramethyl-18,19-epoxytricosa-8,12,14-trien-11-olide; (8E,12E,14E)-3,6,7-trihydroxy-6,10,12,16,20-pentamethyl-21-oxo-18,19-epoxytricosa-8,12,14-trien-11-olide; a 3-position isomer of (8E,12E,14E)-7-acetoxy-3,6,21-trihydroxy-6,10,12,16,20-pentamethyl-18,19-epoxytricosa-8,12,14-trien-11-olide; (8E,12E,14E)-7-acetoxy-3,6,21-trihydroxy-10,12,16,20-tetramethyl-18,19-epoxytricosa-8,12,14-trien-11-olide; (8E,12E,14E)-6-acetoxy-3,7,21-trihydroxy-10,12,16,20-tetramethyl-18,19-epoxytricosa-8,12,14-trien-11-olide; (8E,12E,14E)-3,6,7,21-tetrahydroxy-2,6,10,12,16,20-hexamethyl-18,19-epoxytricosa-8,12,14-trien-11-olide; (8E,12E,14E)-3,7,21-trihydroxy-10,12,16,20-tetramethyl-18,19-epoxytricosa-8,12,14-trien-11-olide; (4E,8E,12E,14E)-7-acetoxy-3,6-dihydroxy-6,10,12,16,20-pentamethyl-21-oxo-18,19-epoxytricosa-4,8,12,14-tetraen-11-olide; (8E,12E,14E)-7-acetoxy-3,21-dihydroxy-10,12,16,20-tetramethyl-18,19-epoxy-6,6-(epoxymethano)tricosa-8,12,14-trien-11-olide; (4E,8E,12E,14E)-7-acetoxy-3,21-dihydroxy-10,12,16,20-tetramethyl-18,19-epoxy-6,6-(epoxymethano)tricosa-4,8,12,14-tetraen-11-olide; (8E,12E,14E)-3,7,21-trihydroxy-10,12,16,20-tetramethyl-18,19-epoxy-6,6-(epoxymethano)tricosa-8,12,14-trien-11-olide; (4E,8E,12E,14E)-6,7-diacetoxy-3,21-dihydroxy-6,10,12,16,20-pentamethyl-18,19-epoxytricosa-4,8,12,14-tetraen-11-olide; (8E,12E,14E)-6,7-diacetoxy-3,21-dihydroxy-6,10,12,16,20-pentamethyl-18,19-epoxytricosa-8,12,14-trien-11-olide; (8E,12E,14E)-7-acetoxy-3,6,16-trihydroxy-6,10,12,16,20-pentamethyl-21-oxo-18,19-epoxytricosa-8,12,14-trien-11-olide; (8E,12E,14E)-7-acetoxy-3,6,21,22-tetrahydroxy-6,10,12,16,20-pentamethyl-18,19-epoxytricosa-8,12,14-trien-11-olide; (4E,8E,12E,14E)-7-acetoxy-3,6,17,21-tetrahydroxy-6,10,12,16,20-pentamethyl-18,19-epoxytricosa-4,8,12,14-tetraen-11-olide; (8E,12E,14E)-7-acetoxy-3,6,17-trihydroxy-6,10,12,16-tetramethyl-18,19-epoxyheneicosa-8,12,14-trien-11-olide; (8E,12E,14E)-7-acetoxy-3,5,6,21,22-pentahydroxy-6,10,12,16,20-pentamethyl-18,19-epoxytricosa-8,12,14-trien-11-olide; (8E,12E,14E)-7-acetoxy-3,6,16-trihydroxy-6,10,12,16-tetramethyl-18,19-epoxyheneicosa-8,12,14-trien-11-olide; (8E,12E,14E)-3,6,7,21-tetrahydroxy-6,10,16,20-tetramethyl-18,19-epoxytricosa-8,12,14-trien-11-olide; (8E,12E,14E)-7-acetoxy-3,6,17,21-tetrahydroxy-6,10,12,16,20-pentamethyl-18,19-epoxytricosa-8,12,14-trien-11-olide; (8E,12E,14E)-7-acetoxy-3,6,17-trihydroxy-6,10,12,16,18-pentamethyl-18,19-epoxyheneicosa-8,12,14-trien-11-olide; and (8E,12E,14E)-7-acetoxy-3,6,21-trihydroxy-6,10,12,16,20-pentamethyl-5-oxo-18,19-epoxytricosa-8,12,14-trien-11-olide.

Specific examples of the macrolide compound expressed by the formula (1-2) include (8E,12E,14E,18E)-7-acetoxy-3,6,21,22-tetrahydroxy-6,10,12,16,20-pentamethyltricosa-8,12,14,18-tetraen-11-olide and (8E,12E,14E,18E)-7-acetoxy-3,6,21-trihydroxy-6,10,12,16,20-pentamethyltricosa-8,12,14,18-tetraen-11-olide.

Examples of the cyclodextrin used in the stabilization method of the present invention include α-cyclodextrin, β-cyclodextrin, γ-cyclodextrin, hexakis (2,3,6-tri-O-acetyl)-α-cyclodextrin, heptakis(2,3,6-tri-O-acetyl)-β-cyclodextrin, octakis (2,3,6-tri-O-acetyl)-γ-cyclodextrin, acetylated α-cyclodextrin, acetylated β-cyclodextrin, acetylated γ-cyclodextrin, hexakis(2,3,6-tri-O-methyl)-α-cyclodextrin, heptakis(2,3,6-tri-O-methyl)-β-cyclodextrin, octakis(2,3,6-tri-O-methyl)-γ-cyclodextrin, heptakis(2,6-di-O-methyl)-β-cyclodextrin, partially methylated α-cyclodextrin, partially methylated β-cyclodextrin, partially methylated γ-cyclodextrin, heptakis(2,6-di-O-methyl)-β-cyclodextrin, 2-O-(2-hydroxy)propyl-α-cyclodextrin, 2-O-(2-hydroxy)propyl-β-cyclodextrin, 2-O-(2-hydroxy)propyl-γ-cyclodextrin, (2-hydroxy)propyl-α-cyclodextrin, (2-hydroxy)propyl-β-cyclodextrin, (2-hydroxy)propyl-γ-cyclodextrin, carboxylmethylated α-cyclodextrin, carboxylmethylated β-cyclodextrin, carboxylmethylated γ-cyclodextrin, succinylated α-cyclodextrin, succinylated β-cyclodextrin, succinylated γ-cyclodextrin, heptakis (3-O-allyl-2,6-di-O-methyl)-β-cyclodextrin, carboxylethylated α-cyclodextrin, carboxylethylated β-cyclodextrin, carboxylethylated γ-cyclodextrin, hexakis(2,6-di-O-n-pentyl)-α-cyclodextrin, heptakis(2,6-di-O-n-pentyl)-β-cyclodextrin, octakis (2,6-di-O-n-pentyl)-γ-cyclodextrin, hexakis(3-O-n-butyl-2,6-di-2-n-pentyl)-α-cyclodextrin, heptakis(3-O-n-butyl-2,6-di-O-n-pentyl)-β-cyclodextrin, octakis (3-O-n-butyl-2,6-di-O-n-pentyl)-γ-cyclodextrin, heptakis(2,6-di-O-n-butyl)-β-cyclodextrin, n-butylated α-cyclodextrin, n-butylated β-cyclodextrin, n-butylated γ-cyclodextrin, hexakis (2,3,6-tri-O-benzoyl)-α-cyclodextrin, heptakis(2,3,6-tri-O-benzoyl)-β-cyclodextrin, octakis (2,3,6-tri-O-benzoyl)-γ-cyclodextrin, palmitoylated β-cyclodextrin, 6-O-monotosylated β-cyclodextrin, ethylated α-cyclodextrin, ethylated β-cyclodextrin, ethylated γ-cyclodextrin, heptakis(2,6-di-O-ethyl)-β-cyclodextrin, hexakis(2,3,6-tri-O-ethyl)-α-cyclodextrin, heptakis(2,3,6-tri-O-ethyl)-β-cyclodextrin, octakis(2,3,6-tri-O-ethyl)-γ-cyclodextrin, 6-monodeoxy-6-monoamino-β-cyclodextrin hydrochloride, hexakis(3-O-acetyl-2,6-di-O-n-pentyl)-α-cyclodextrin, heptakis(3-O-acetyl-2,6-di-O-n-pentyl)-β-cyclodextrin, octakis(3-O-acetyl-2,6-di-O-n-pentyl)-γ-cyclodextrin, hexakis(2,6-di-O-n-pentyl-3-O-trifluoroacetyl)-α-cyclodextrin, heptakis(2,6-di-O-n-pentyl-3-O-trifluoroacetyl)-β-cyclodextrin, octakis(2,6-di-O-n-pentyl-3-O-trifluoroacetyl)-γ-cyclodextrin, hexakis(2,6-di-O-methyl-3-O-n-pentyl)-α-cyclodextrin, heptakis(2,6-di-O-methyl-3-O-n-pentyl)-β-cyclodextrin, octakis (2,6-di-O-methyl-3-O-n-pentyl)-γ-cyclodextrin, (2-hydroxy)ethylated α-cyclodextrin, (2-hydroxy)ethylated β-cyclodextrin, (2-hydroxy)ethylated γ-cyclodextrin, hexakis(2,3,6-tri-O-n-octyl)-α-cyclodextrin, heptakis(2,3,6-tri-O-n-octyl)-β-cyclodextrin, octakis (2,3,6-tri-O-n-octyl)-γ-cyclodextrin, hexakis (2,3-di-O-acetyl-6-O-tert-butyldimethylsilyl)-α-cyclodextrin, heptakis(2,3-di-O-acetyl-6-O-tert-butyldimethylsilyl)-β-cyclodextrin, octakis(2,3-di-O-acetyl-6-O-tert-butyldimethylsilyl)-γ-cyclodextrin, succinylated (2-hydroxy)propyl-α-cyclodextrin, succinylated (2-hydroxy)propyl-β-cyclodextrin, succinylated (2-hydroxy)propyl-γ-cyclodextrin, hexakis(6-O-tert-butyldimethylsilyl)-α-cyclodextrin, heptakis(6-O-tert-butyldimethylsilyl)-β-cyclodextrin, octakis(6-O-tert-butyldimethylsilyl)-γ-cyclodextrin, hexakis(6-O-tert-butyldimethylsilyl-2,3-di-O-methyl)-α-cyclodextrin, heptakis(6-O-tert-butyldimethylsilyl-2,3-di-O-methyl)-β-cyclodextrin, octakis (6-O-tert-butyldimethylsilyl-2,3-di-O-methyl)-γ-cyclodextrin, hexakis(2,6-di-O-tert-butyldimethylsilyl)-α-cyclodextrin, heptakis(2,6-di-O-tert-butyldimethylsilyl)-β-cyclodextrin, octakis(2,6-di-O-tert-butyldimethylsilyl)-γ-cyclodextrin, octamesitylene-γ-cyclodextrin, hexakis(2,3,6-tri-O-trifluoroacetyl)-α-cyclodextrin, heptakis(2,3,6-tri-O-trifluoroacetyl)-β-cyclodextrin, octakis(2,3,6-tri-O-trifluoroacetyl)-γ-cyclodextrin, sulfopropylated α-cyclodextrin, sulfopropylated β-cyclodextrin, sulfopropylated γ-cyclodextrin, 6-O-monomaltosyl-β-cyclodextrin, 6-O-maltosyl-β-cyclodextrin, (2-carbomethoxy)propoxy-β-cyclodextrin, heptakis(3-O-acetyl-2,6-di-O-n-butyl)-β-cyclodextrin, (2-cyano)ethyl-α-cyclodextrin, (2-cyano)ethyl-β-cyclodextrin, (2-cyano)ethyl-γ-cyclodextrin, 6-monodeoxy-6-monoazido-β-cyclodextrin, 6-monodeoxy-6-monoiodo-β-cyclodextrin, 6A,6B-dideoxy-6A,6B-diiodo-β-cyclodextrin, 6-monodeoxy-6-monobromo-β-cyclodextrin and 6A,6B-dideoxy-6A,6B-dibromo-β-cyclodextrin.

Of these cyclodextrins, a cyclodextrin selected from the group consisting of β-cyclodextrin, γ-cyclodextrin, partially methylated β-cyclodextrin, dimethyl-β-cyclodextrin, glycosyl-β-cyclodextrin and hydroxypropyl-β-cyclodextrin is preferable. These cyclodextrins can be used singly or in combinations of two or more.

(Method for Producing Macrolide Compound)

In the method for producing a macrolide compound of the present invention, a cyclodextrin is made to be present in a culture broth of actinomycetes having an ability of producing a macrolide compound selected from the above-mentioned macrolide compound (2) group.

The macrolide compound selected from the macrolide compound (2) group is preferably (8E,12E,14E)-7-acetoxy-3,6,21-trihydroxy-6,10,12,16,20-pentamethyl-18,19-epoxytricosa-8,12,14-trien-11-olide (macrolide compound 11107B).

There are no particular restrictions on the actinomycetes having an ability of producing the macrolide compound, as long as they are indeed actinomycetes having an ability of producing a macrolide compound, but examples include actinomycetes belong to the genus *Streptomyces*, and particularly *Streptomyces* sp. Mer-11107 isolated from soil, or *Streptomyces* sp. A-1532, *Streptomyces* sp. A-1533, *Streptomyces* sp. A-1534, etc., which are variants of Mer-11107.

It is to be noted that the *Streptomyces* sp. Mer-11107 was deposited as International Deposit FERM BP-7812 as of Nov. 27, 2001, the *Streptomyces* sp. A-1532 was deposited as International Deposit FERM BP-7849 as of Jan. 18, 2002, the *Streptomyces* sp. A-1533 was deposited as International Deposit FERM BP-7850 as of Jan. 18, 2002, and the *Streptomyces* sp. A-1534 was deposited as International Deposit FERM BP-7851 as of Jan. 18, 2002, each at International Patent Organism Depositary (IPOD) National Institute of Advanced Industrial Science and Technology (Tsukuba Central 6, 1-1, Higashi 1-Chome, Tsukuba-shi, Ibaraki-ken 305-8566 Japan).

The properties of the microbes used in the present invention to produce the macrolide compound, in particular Mer-11107 strain, the culture method and the method for purifying the macrolide compound, will now be described in detail.

1. Taxonomical Properties of the Mer-11107 Strain (1) Morphological Characteristics Spirales type aerial hyphae were extended from the vegetative hyphae. Spore chains consisting of about 10 to 20 cylindrical spores were formed at the end of the matured aerial hyphae. The size of the spores was about 0.7×1.0 μm, the surface of the spores was smooth, and specific organs such as sporangium, sclerotium and flagellum were not observed.

(2) Cultural Characteristics on Various Media

Cultural characteristics of the strain after incubation at 28° C. for two weeks on various media are shown as follows. The color tone is described by the color names and codes which are shown in the parentheses of Tresner's Color wheels.

1) Yeast Extract-Malt Extract Agar Medium

The strain grew well, the aerial hyphae grew up on the surface, and light gray spores (Light gray; d) were observed. The reverse side of colony was Light melon yellow (3ea). Soluble pigment was not produced.

2) Oatmeal Agar Medium

The strain grew moderately, the aerial hyphae grew slightly on the surface, and gray spores (Gray; g) were observed. The reverse side of colony was Nude tan (4gc) or Putty (1 1/2ec). Soluble pigment was not produced.

3) Inorganic Salts-Starch Agar Medium

The strain grew well, the aerial hyphae grew up on the surface, and gray spores (Gray; e) were observed. The reverse side of colony was Fawn (4ig) or Gray (g). Soluble pigment was not produced.

4) Glycerol-Asparagine Agar Medium

The strain grew well, the aerial hyphae grew up on the surface, and white spores (White; a) were observed. The reverse side of colony was Pearl pink (3ca). Soluble pigment was not produced.

5) Peptone-Yeast Extract-Iron Agar Medium

The strain growth was bad, and the aerial hyphae did not grow on the surface. The reverse side of colony was Light melon yellow (3ea). Soluble pigment was not produced.

6) Tyrosine Agar Medium

The strain grew well, the aerial hyphae grew up on the surface, and white spores (White; a) were observed. The reverse side of colony was Pearl pink (3ca). Soluble pigment was not produced.

(3) Utilization of Various Carbon Sources

Various carbon sources were added to Pridham-Gottlieb agar and incubated 28° C. for 2 weeks. The growth of the strain is shown below.

1) L-arabinose ±

2) D-xylose ±

3) D-glucose +

4) D-fructose +

5) Sucrose +

6) Inositol +

7) L-rhamnose −

8) D-mannitol +

9) Raffinose +

(+ positive, ± slightly positive, − negative)

(4) Various Physiological Properties

Various physiological properties of the present strain are as follows.

(a) Range of growth temperature (yeast extract-malt extract agar, incubation for 2 weeks): 12° C. to 37° C.

(b) Range of optimum growth temperature (yeast extract-malt extract agar, incubation for 2 weeks): 21° C. to 33° C.

(c) Liquefaction of gelatin (glucose-peptone-gelatin medium): negative (d) Coagulation of milk (skim milk medium): negative (e) Peptonization of milk (skim milk medium): negative (f) Hydrolysis of starch (inorganic salts-starch agar): positive (g) Formation of melanoid pigment (peptone-yeast extract-iron agar): negative (tyrosine agar): negative (h) Production of hydrogen sulfide (peptone-yeast extract-iron agar): negative (i) Reduction of nitrate (broth containing 0.1% potassium nitrate): negative (j) Sodium chloride tolerance (yeast extract-malt extract agar, incubation for 2 weeks): grown at a salt content of 4% or less (5) Chemotaxonomy LL-diaminopimelic acid was detected from the cell wall of the present strain.

2. Fermentation Method of Producing Microorganism

The macrolide compound according to the present invention can be produced by inoculating the strain on a nutrition source medium and fermenting aerobically.

The fermentation method of the above-mentioned microorganism is according to the general fermentation method of microorganism, except that a cyclodextrin is made to be present. It is preferably carried out under aerobic conditions such as shaking culture or aeration-agitation fermentation using liquid medium. The medium used for culture may be a medium containing a nutrition source which can be utilized by microorganism belonging to the genus Streptomyces, therefore all of various synthetic, a semi-synthetic medium, an organic medium and the like can be utilized. As the carbon source in the medium composition, there can be used a single or a combination of glucose, sucrose, fructose, glycerin, dextrin, starch, molasses, soybean oil and the like. As the nitrogen source, there can be used a single or a combination of organic nitrogen sources such as pharma media, peptone, meat extract, soybean meal, casein, amino acid, yeast extract and urea, and inorganic nitrogen sources such as sodium nitrate and ammonium sulfate. Additionally, for example, there can be added and used salts such as sodium chloride, potassium chloride, calcium carbonate, magnesium sulfate, sodium phosphate, potassium phosphate and cobalt chloride; heavy metal salts, vitamins such as vitamin B or biotin, if necessary.

In the present invention, a cyclodextrin is made to be present in the above-mentioned culture broth. The concentration of the cyclodextrin in the culture broth may be suitably selected within a range that will not impair the growth of the microorganism being used, and is preferably from 0.1 to 100 mg/mL, with 10 to 30 mg/mL being even better.

There are no particular restrictions on the point when the cyclodextrin is added, which may be either before or after the culture medium is inoculated with the microbes that produce the macrolide compound, but it is preferable to add the cyclodextrin to the medium before the macrolide compound-producing microbes produce the targeted substance.

Examples of the cyclodextrin used in the producing method of the present invention are those listed in the section dealing with the method for stabilizing a macrolide compound above, but it is preferable to select from the group comprising β-cyclodextrin, γ-cyclodextrin, partially methylated β-cyclodextrin, dimethyl-β-cyclodextrin, glucosyl-β-cyclodextrin, and hydroxypropyl-β-cyclodextrin. These cyclodextrins can be used singly or in combinations of two or more.

When foaming is occurred during fermentation, any of various defoaming agents can be added to the medium as necessary. In adding a defoaming agent, the concentration must be set low enough so that the agent will not have an inordinately adverse effect on the production of the targeted substance, and using the agent in a concentration of 0.3% or less is preferable, for example.

The conditions of fermentation can be appropriately selected within a range over which this microbial strain will grow well and can produce the above-mentioned substance. For instance, the pH of a medium is about 5 to 9, and preferably nearby neutral in general. The temperature of fermentation is usually kept between 20 and 40° C., and preferably between 28 and 35° C. The fermentation period is about 2 to 8 days, and usually about 3 to 6 days. The above fermentation conditions can be suitably changed in accordance with the kind and properties of microorganism used, external conditions and the like, and it is needless to say that the optimum conditions can be selected. The macrolide compound that accumulates in the culture broth can be recovered by an ordinary separation process that is suited to the properties thereof, such as solvent extraction or the use of an adsorbent resin.

3. Purification of Macrolide Compound

Any separation and purification methods which are commonly used for isolating microbial metabolites from their culture broth can be utilized to collect the macrolide compound from the culture broth after fermentation. It is possible to employ any other known method, for example, (1) organic solvent extraction using methanol, ethanol, butanol, ethyl acetate, butyl acetate, toluene, chloroform or the like, (2) an adsorption and desorption treatment using a hydrophobic adsorbent resin such as Diaion, HP-20 or the like, (3) various kinds of ion exchange chromatography, (4) gel filtration chromatography using Sephadex LH-20 or the like, (5) activated carbon, (6) adsorption chromatography using silica gel or the like, or an adsorption and desorption treatment by thin layer chromatography or (7) high performance liquid chromatography using a reverse phase column or the like. The purification methods are not limited to those listed here.

A macrolide compound can be isolated and refined by using these methods alone, or by combining them in any order desired, or by employing them repeatedly.

The stabilization method of the present invention allows a macrolide compound to be stabilized in the solid phase or in solution. Also, the producing method of the present invention allows a macrolide compound to be produced efficiently.

EXAMPLES

The present invention will now be described in specific terms by giving Examples, but the present invention is not limited in any way by these examples. In the following description, all concentrations given are in volume percent unless otherwise specified.

Example 1

Effects of Various Cyclodextrins on Stabilization of Macrolide Compound

The macrolide compound 11107B (hereinafter sometimes abbreviated as 11107B) and various cyclodextrins were dissolved in concentrations of 0.1 mg/mL and 10 mg/mL, respectively, in Dulbecco's PBS (−). The 11107B solution and cyclodextrin solution were mixed in equal volumes, and incubation was immediately begun in at thermostatic incubator at 25° C. The solution was sampled at the start (0 hour) and after 24 and 48 hours had elapsed, the samples were analyzed by high performance liquid chromatography (HPLC) under the following analysis conditions (A), and the purity of the 11107B was calculated from the following equation using the chromatogram thus obtained.

These results are given in Table 1. It can be seen from these results that of the cyclodextrins examined, β-cyclodextrin has the best stabilizing effect.

<Types of Cyclodextrin>
α-CD: α-cyclodextrin
β-CD: β-cyclodextrin
γ-CD: γ-cyclodextrin
HP-α-CD: hydroxypropyl-α-cyclodextrin
HP-β-CD: hydroxypropyl-β-cyclodextrin
HP-γ-CD: hydroxypropyl-γ-cyclodextrin
<HPLC Analysis Conditions (A)>

Column: L-column, 4.6×150 mm, Chemicals Evaluation and Research Institute

Column temperature: 35° C.

Flow rate: 1 mL/min

Detection wavelength: 241 nm

Mobile phase A: 0.1% (v/v) formic acid•10% (v/v) acetonitrile

Mobile phase B: 0.1% (v/v) formic acid•90% (v/v) acetonitrile

Gradient program: B=10% (start)→B=40% (15 minutes)→B=100% (20 minutes)→B=10% (20.01 minutes)→B=10% (23 minutes, stop)<

<Calculation Equation>

11107B purity(%)=[peak surface area value of 11107B/(sum of peak surface area value of 11107B+peak surface area value of impurities and decomposition products)]×100

TABLE 1

| Time | Purity of macrolide compound 11107B (%) | | | | | | |
|---|---|---|---|---|---|---|---|
| (h) | CD not added | α-CD | β-CD | γ-CD | HP-α-CD | HP-β-CD | HP-γ-CD |
| 0 | 99 | 99 | 100 | 100 | 99 | 100 | 99 |
| 24 | 62 | 71 | 95 | 88 | 71 | 93 | 83 |
| 48 | 35 | 47 | 90 | 77 | 47 | 86 | 67 |

Example 2

Calculation of Stabilization Coefficients of Macrolide Compound 11107B and β-Cyclodextrin (Cyclodextrin Will Hereinafter be Abbreviated as CD)

The macrolide compound 11107B was dissolved in Dulbecco's PBS (−) in a concentration of 0.1 mg/mL, and β-CD in concentrations of 10, 3, 1, and 0.3 mg/mL. The 11107B solution and β-CD solution were mixed in equal volumes, and incubation was immediately begun in a 40° C. thermostatic incubator. The solution was sampled at the start (0 hour) and after 1, 2, 4 and 6 hours had elapsed, the samples were analyzed by HPLC under the analysis conditions (A) of Example 1, and the concentration of the 11107B was calculated. Since the plot of the 11107B concentration versus elapsed time was substantially linear, it was concluded that decomposition was occurring in pseudo first-order reaction, and the apparent decomposition rate constant $k_{obs}$ was calculated from the slope thereof. $k_{obs}$ was termed $k_0$ when no β-CD was prevent. According to a report by Ma et al. (J. Pharm. Sci. (2000), 89 (2), 275-287), $1/(k_0-k_{obs})$ was plotted against the inverse of the β-CD concentration, kc, which is $k_{obs}$ when a large excess of β-CD was present, was calculated from an intercept thereof, and the stabilization constant Kc was calculated from the slope.

Figure 1:
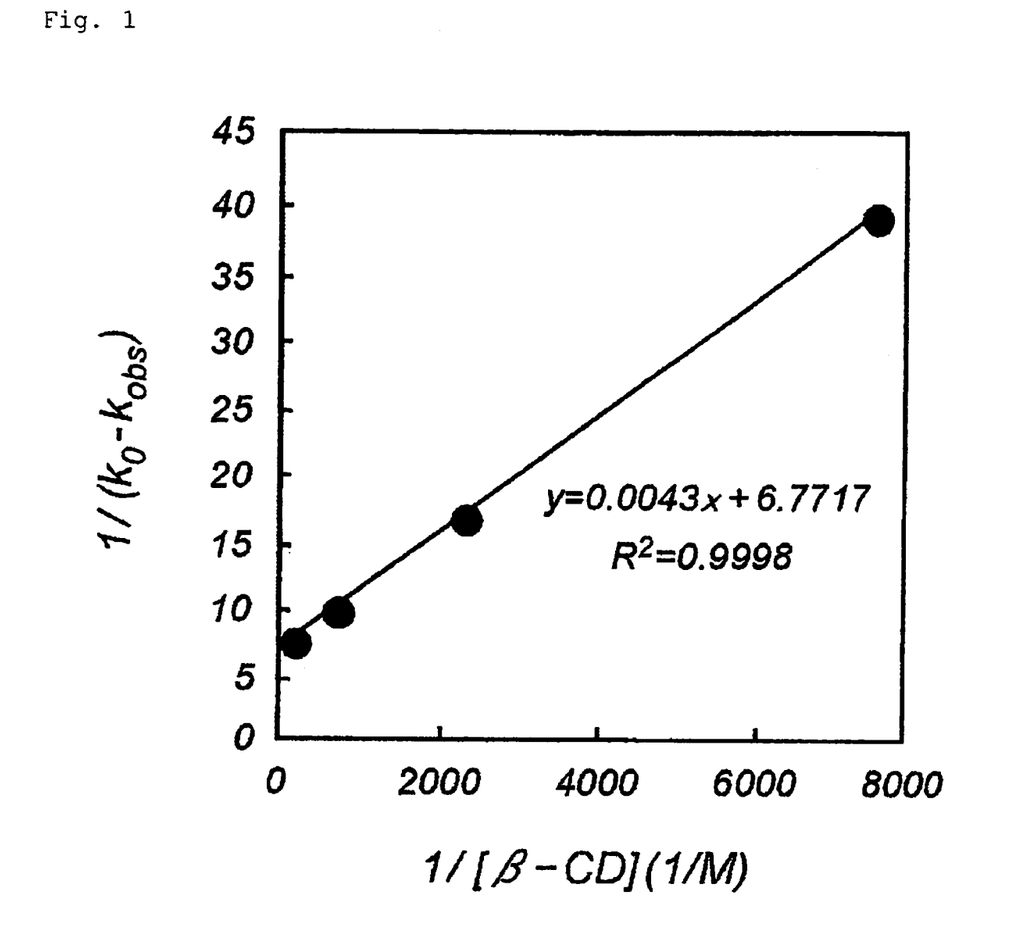
FIG. 1 shows the results of plotting $1/(k_0-k_{obs})$ versus the inverse of the β-cyclodextrin concentration, as obtained in Example 2.

The results are given in Table 2 and FIG. 1. These results show that $k_0$ and kc were estimated to be 0.152 $hr^{-1}$ and 0.004 $hr^{-1}$, respectively, and that the decomposition rate of included 11107B was $\frac{1}{30}^{th}$ or less than that of 11107B that was not included. Also, since Kc was estimated to be 1500 or more, this shows that, in the solution of 11107B with equal molar ratio of β-CD, almost all of the 11107B include in β-CD.

TABLE 2

| β-CD concentration (mg/mL) | 0 | 5 | 1.5 | 0.5 | 0.15 |
|---|---|---|---|---|---|
| $k_{obs}$ (hr$^{-1}$) | 0.152 | 0.020 | 0.052 | 0.092 | 0.126 |
| $k_0 - k_{obs}$ | — | 0.132 | 0.100 | 0.060 | 0.026 |
| $1/(k_0 - k_{obs})$ | — | 7.590 | 9.971 | 16.736 | 39.057 |

Example 3

Effect of β-CD and methylated β-CD on Stabilization of Macrolide Compound

The macrolide compound 11107B and β-CD or methylated β-CD were dissolved in Dulbecco's PBS (−) in concentrations of 0.1 mg/mL and 10 mg/mL, respectively. The 11107B solution and β-CD solution were mixed in equal volumes, and incubation was immediately begun in thermostatic incubator at 25° C. The solution was sampled at the start (0 hour) and after 24, 48 and 120 hours had elapsed, and the samples were analyzed by HPLC under the following analysis conditions (B). The purity of the 11107B was calculated from the equation in Example 1 using the resulting chromatogram.

<HPLC Analysis Conditions (B)>

Column: Develosil ODS UG-3, 4.6×50 mm, 3 μm (made by Nomura Chemical)

Column temperature: 40° C.

Flow rate: 1.2 mL/min

Detection wavelength: 240 nm

Eluate: water/methanol gradient
A=water, B=methanol
45-55% B (0 to 5 minutes), 55% B (5 to 13 minutes)
55-70% B (13 to 21 minutes), 45% B (21 to 25 minutes)

Retention time: 13 minutes (11107B)

These results are given in Table 3. The methylated β-CD had the same or better stabilization effect as the β-CD.

TABLE 3

| Time | Purity of macrolide compound 11107B (%) | | |
|---|---|---|---|
| (h) | CD not added | β-CD | methylated β-CD |
| 0 | 98 | 98 | 98 |
| 24 | 59 | 95 | 95 |
| 48 | 34 | 90 | 92 |
| 120 | 3 | 74 | 80 |

Example 4

Effect of Adding α-, β- and γ-CD to Culture Broth 60 mL of culture medium containing soluble starch 2%, soybean meal (ESUSAN-MEAT manufactured by Ajinomoto Co. Ltd.) 2%, yeast extract (made by Oriental Yeast) 0.3%, dipotassium phosphate 0.1%, magnesium sulfate heptahydrate 0.25% and calcium carbonate 0.3% was poured into 500 mL Erlenmeyer flasks and then sterilized to prepare a seed medium. This seed medium was inoculated with 0.6 mL of frozen seed of *Streptomyces* sp. Mer-11107 (FERM BP-7812), and incubated at 25° C. for 2 days on a rotary shaker at 220 rpm to give a seed culture broth. A medium containing soluble starch 5%, Pharmamedia 3% and calcium carbonate 0.1% was prepared, and then adjusted to pH of 7.5 by sodium hydroxide. The medium was poured into 250 mL Erlenmeyer flasks by 30 mL, α-, β- and γ-CD were added in the concentrations shown in Table 4, and then it was sterilized. Then, pre-sterilized glucose was added in an amount of 1%, to prepare a producing medium. 0.3 mL of the above-mentioned seed culture broth was inoculated with the medium and incubated at 25° C. for 5 days on a rotary shaker at 220 rpm. This culture broth was diluted 6 times with methanol, and then it was analyzed by HPLC under the analysis conditions (B) of Example 3 to assay the 11107B substance. These results are given in Table 4.

TABLE 4

| Additive and additive concentration | Amount of 11107B (μg/mL) |
|---|---|
| α-CD 1% | 315 |
| α-CD 2% | 340 |
| α-CD 3% | 337 |
| β-CD 1% | 567 |
| β-CD 2% | 1039 |
| β-CD 3% | 1060 |
| γ-CD 1% | 568 |
| γ-CD 2% | 689 |
| γ-CD 3% | 727 |
| CD not added | 272 |

Example 5

Effect of Adding Various Kinds of β-CD to Culture Broth 60 mL of culture medium containing soluble starch 2%, soybean meal (ESUSAN-MEAT manufactured by Ajinomoto Co. Ltd.) 2%, yeast extract (made by Oriental Yeast) 0.3%, dipotassium phosphate 0.1%, magnesium sulfate heptahydrate 0.25% and calcium carbonate 0.3% was poured into 500 mL Erlenmeyer flasks and then sterilized to prepare a seed medium. This seed medium was inoculated with 0.6 mL of frozen seed of *Streptomyces* sp. Mer-11107 (FERM BP-7812), and incubated at 25° C. for 2 days on a rotary shaker at 220 rpm to give a seed culture broth. A medium containing soluble starch 5%, Pharmamedia 3% and calcium carbonate 0.1% was prepared, and then adjusted to pH of 7.5 by sodium hydroxide. The medium was poured into 250 mL Erlenmeyer flasks by 30 mL, the various kinds of β-CD derivative shown in Table 5 were added in a concentration of 2%, and then it was sterilized. Then, pre-sterilized glucose was added in an amount of 1%, to prepare a producing medium. 0.3 mL of the above-mentioned seed culture broth was inoculated with the medium and incubated at 25° C. for 5 days on a rotary shaker at 220 rpm. This culture broth was diluted 6 times with methanol, and then it was analyzed by HPLC under the analysis conditions (B) of Example 3 to assay the 11107B substance. These results are given in Table 5.

TABLE 5

| Additive | Amount of 11107B (μg/mL) |
|---|---|
| β-CD | 823 |
| methylated β-CD | 848 |
| dimethylated β-CD | 920 |
| trimethylated β-CD | 387 |
| glycosyl β-CD | 737 |
| hydroxypropyl-β-CD | 703 |
| isoeleat P* | 402 |
| CD not added | 254 |

*Cyclodextrin mixture (made by Ensuiko Sugar Refining; total cyclodextrin content: at least 80%, containing at least 50% maltosyl cyclodextrin)

Example 6

Purification of Macrolide Compound 11107B from Culture Broth to which β-CD was Added 60 mL of culture medium containing soluble starch 2%, soybean meal (ESUSAN-MEAT manufactured by Ajinomoto Co. Ltd.) 2%, yeast extract (made by Oriental Yeast) 0.3%, dipotassium phosphate 0.1%, magnesium sulfate heptahydrate 0.25% and calcium carbonate 0.3% was poured into 500 mL Erlenmeyer flasks and then sterilized to prepare a seed medium. This seed medium was inoculated with 0.6 mL of frozen seed of *Streptomyces* sp. Mer-11107 (FERM BP-7812), and incubated at 25° C. for 2 days on a rotary shaker at 220 rpm to give a seed culture broth. A medium containing soluble starch 5%, Pharmamedia 3% and calcium carbonate 0.1% was prepared, and then adjusted to pH of 7.5 by sodium hydroxide. 60 mL of this medium was poured into 500 mL Erlenmeyer flasks, β-CD was added in a concentration of 2%, and then the medium was sterilized. Further, pre-sterilized glucose was added in an amount of 1% to prepare a producing medium. 0.6 mL of the above-mentioned seed culture broth was inoculated with the medium and incubated at 25° C. for 5 days on a rotary shaker at 220 rpm.

The resulting culture broth was put in a centrifuge tube and centrifuged for 10 minutes at 3500 rpm to separate the supernatant from the mycelia. 60 mL of the supernatant was extracted with 60 mL of toluene. The toluene layer was dried over anhydrous sodium sulfate and then the toluene was evaporated, to give 0.1012 g of a crude 11107B as an oil. The crude 11107B was purified by TLC (Merck Art. 105717, toluene:acetone=2:1), to give 84.3 mg of 11107B as an oil.

$^1$H-NMR spectrum (CD$_3$OD, 500 MHz): δ ppm (integral, multiplicity, coupling constant J (Hz)): 0.93 (3H, d, J=7.0 Hz), 0.94 (3H, d, J=6.8 Hz), 0.98 (3H, t, J=8.0 Hz), 1.12 (3H, d, J=6.8 Hz), 1.23 (3H, s), 1.25 (1H, m), 1.42 (2H, m), 1.53-1.70 (6H, m), 1.79 (3H, d, J=1.0 Hz), 2.10 (3H, s), 2.52 (1H, m), 2.56 (2H, m), 2.60 (1H, m), 2.70 (1H, dd, J=2.4, 8.3 Hz), 2.76 (1H, dt, J=2.4, 5.7 Hz), 3.56 (1H, dt, J=8.3, 4.4 Hz), 3.82 (1H, m), 5.08 (2H, d, J=9.8 Hz), 5.60 (1H, dd, J=9.8, 15.2 Hz), 5.70 (1H, dd, J=8.3, 15.2 Hz), 5.74 (1H, dd, J=9.8, 15.2 Hz), 6.13 (1H, d, J=9.8 Hz), 6.36 (1H, dd, J=9.8, 15.2 Hz)

Example 7

Stabilizing Effect of HP-β-CD on Macrolide Compound 11107B in Freeze-Dried Preparation Lactose monohydrate was dissolved in purified water in a concentration of 10 mg/mL and HP-β-CD in concentrations of 0, 10 and 200 mg/mL. The macrolide compound 11107B was dissolved in a concentration of 0.1 mg/mL in each of these three types of solution. 1 mL of each solution was put into vials and freeze-dried. The freeze-dried preparations thus obtained were stored for one month at −20° C., 40° C. and 60° C., after which 1 mL of 50% acetonitrile aqueous solution was added to each vial to dissolve the preparation. This product was analyzed by HPLC analysis under the conditions (A) of Example 1, and the purity of the 11107B was calculated according to the equation of Example 1. These results are given in Table 6.

TABLE 6

| Storage temperature (° C.) | Purity of macorolide compound 11107B (%) | | |
| --- | --- | --- | --- |
| | HP-β-CD not added | HP-β-CD concentration (10 mg/mL) | HP-β-CD concentration (200 mg/mL) |
| −20 | 99.56 ± 0.01 | 99.73 ± 0.01 | 99.70 ± 0.00 |
| 40 | 98.17 ± 0.12 | 99.76 ± 0.08 | 99.82 ± 0.02 |
| 60 | 94.63 ± 0.11 | 98.60 ± 0.06 | 98.90 ± 0.05 |

It is clear from the above results that the addition of cyclodextrin sufficiently stabilized the macrolide compound 11107B even in a solid form in a freeze-dried preparation.

The invention claimed is:
1. A method for producing a macrolide compound selected from the group consisting of (8E,12E,14E)-3,6,7,21-tetrahydroxy-6,10,12,16,20-pentamethyl-18,19-epoxytricosa-8,12,14-trien-11-olide; (8E,12E,14E)-7-acetoxy-3,6,21-trihydroxy-6,10,12,16,20-pentamethyl-18,19-epoxytricosa-8,12,14-trien-11-olide; (8E,12E,14E)-7-acetoxy-3,6-dihydroxy-6,10,12,16,20-pentamethyl-21-oxo-18,19-epoxytricosa-8,12,14-trien-11-olide; (8E,12E,14E)-7-acetoxy-3,6,16,21-tetrahydroxy-6,10,12,16,20-pentamethyl-18,19-epoxytricosa-8,12,14-trien-11-olide; (8E,12E,14E)-7-acetoxy-3,6,20,21-tetrahydroxy-6,10,12,16,20-pentamethyl-18,19-epoxytricosa-8,12,14-trien-11-olide; (8E,12E,14E)-3,6,7,16,21-pentahydroxy-6,10,12,16,20-pentamethyl-18,19-epoxytricosa-8,12,14-trien-11-olide; (8E,12E,14E)-3,6,7,20,21-pentahydroxy-6,10,12,16,20-pentamethyl-18,19-epoxytricosa-8,12,14-trien-11-olide; (4E,8E,12E,14E)-7-acetoxy-3,6,21-trihydroxy-6,10,12,16,20-pentamethyl-18,19-epoxytricosa-4,8,12,14-tetraen-11-olide; (8E,12E,14E)-3,6,21-trihydroxy-6,10,12,16,20-pentamethyl-7-propanoyloxy-18,19-epoxytricosa-8,12,14-trien-11-olide; (8E,12E,14E)-7-acetoxy-3,6,21-trihydroxy-6,10,12,16,20-pentamethyl-18,19-epoxydocosa-8,12,14-trien-11-olide; (8E,12E,14E)-7-acetoxy-3,5,6,21-tetrahydroxy-6,10,12,16,20-pentamethyl-18,19-epoxytricosa-8,12,14-trien-11-olide; (8E,12E,14E)-5,7-diacetoxy-3,6,21-trihydroxy-6,10,12,16,20-pentamethyl-18,19-epoxytricosa-8,12,14-trien-11-olide; (8E,12E,14E)-3,7-diacetoxy-6,21-dihydroxy-6,10,12,16,20-pentamethyl-18,19-epoxytricosa-8,12,14-trien-11-olide; (8E,12E,14E)-7-acetoxy-6-acetoxymethyl-3,6,21-trihydroxy-10,12,16,20-tetramethyl-18,19-epoxytricosa-8,12,14-trien-11-olide; (8E,12E,14E)-7-acetoxy-3,6,17,21-tetrahydroxy-6,10,12,16,20-pentamethyl-18,19-epoxytricosa-8,12,14-trien-11-olide; (8E,12E,14E)-7-acetoxy-3,6,20-trihydroxy-6,10,12,16-tetramethyl-18,19-epoxyheneicosa-8,12,14-trien-11-olide; (4E,8E,12E,14E)-3,6,7,21-tetrahydroxy-6,10,12,16,20-pentamethyl-18,19-epoxytricosa-4,8,12,14-tetraen-11-olide; (8E,12E,14E)-7-acetoxy-3,6,21-trihydroxy-6,10,12,16-tetramethyl-18,19-epoxytricosa-8,12,14-trien-11-olide; (8E,12E,14E)-7-acetoxy-3,6,21-trihydroxy-6,10,12,20-tetramethyl-18,19-epoxytricosa-8,12,14-trien-11-olide; (12E,14E)-3,6,21-trihydroxy-6,10,12,16,20-pentamethyl-9-oxo-18,19-epoxytricosa-12,14-dien-11-olide; (8E,12E,14E)-7-acetoxy-3,6,21-trihydroxy-6,10,16,20-tetramethyl-18,19-epoxytricosa-8,12,14-trien-11-olide; (8E,12E,14E)-7-acetoxy-3,6,21-trihydroxy-2,6,10,12,16,20-hexamethyl-18,19-epoxytricosa-8,12,14-trien-11-olide; (8E,12E,14E)-7-acetoxy-3,5,21-trihydroxy-6,10,12,16,20-pentamethyl-18,19-epoxytricosa-8,12,14-trien-11-olide; (8E,12E,14E)-7-acetoxy-3,6,21-trihydroxy-6,12,16,20-tetramethyl-18,19-epoxytricosa-8,12,14-trien-11-olide; (8E,12E,14E)-6-acetoxymethyl-3,6,7,2,1-tetrahydroxy-10,12,16,20-tetramethyl-18,19-epoxytricosa-8,12,14-trien-11-olide; (8E,12E,14E)-3,6,7-trihydroxy-6,10,12,16,20-pentamethyl-21-oxo-18,19-epoxytricosa-8,12,14-trien-11-olide; a 3-position isomer of (8E,12E,14E)-7-acetoxy-3,6,21-trihydroxy-6,10,12,16,20-pentamethyl-18,19-epoxytricosa-8,12,14-trien-11-olide; (8E,12E,14E)-7-acetoxy-3,6,21-trihydroxy-10,12,16,20-tetramethyl-18,19-epoxytricosa-8,12,14-trien-11-olide; (8E,12E,14E)-6-acetoxy-3,7,21-trihydroxy-10,12,16,20-tetramethyl-18,19-epoxytricosa-8,12,14-trien-11-olide; (8E,12E,14E)-3,6,7,21-tetrahydroxy-2,6,10,12,16,20-hexamethyl-18,19-epoxytricosa-8,12,14-trien-11-olide; (8E,12E,14E,18E)-7-acetoxy-3,6,21,22-tetrahydroxy-6,10,12,16,20-pentamethyltricosa-8,12,14,18-tetraen-11-olide; (8E,12E,14E)-3,7,21-trihydroxy-10,12,16,20-tetramethyl-18,19-epoxytricosa-8,12,14-trien-11-olide; (4E,8E,12E,14E)-7-acetoxy-3,6-dihydroxy-6,10,12,16,20-pentamethyl-21-oxo-18,19-epoxytricosa-4,8,12,14-tetraen-11-olide; (8E,12E,14E)-7-acetoxy-3,21-dihydroxy-10,12,16,20-tetramethyl-18,19-epoxy-6,6-(epoxymethano)tricosa-8,12,14-trien-11-olide; (4E,8E,12E,14E)-7-acetoxy-3,21-dihydroxy-10,12,16,20-tetramethyl-18,19-epoxy-6,6-(epoxymethano)tricosa-4,8,12,14-tetraen-11-olide; (8E,12E,14E)-3,7,21-trihydroxy-10,12,16,20-tetramethyl-18,19-epoxy-6,6-(epoxymethano)tricosa-8,12,14-trien-11-olide; (4E,8E,12E,14E)-6,7-diacetoxy-3,21-dihydroxy-6,10,12,16,20-pentamethyl-18,19-epoxytricosa-4,8,12,14-tetraen-11-olide; (8E,12E,14E)-6,7-diacetoxy-3,21-dihydroxy-6,10,12,16,20-pentamethyl-18,19-epoxytricosa-8,12,14-trien-11-olide; (8E,12E,14E)-7-acetoxy-3,6,16-trihydroxy-6,10,12,16,20-pentamethyl-21-oxo-18,19-epoxytricosa-8,12,14-trien-11-olide; (8E,12E,14E)-7-acetoxy-3,6,21,22-tetrahydroxy-6,10,12,16,20-pentamethyl-18,19-epoxytricosa-8,12,14-trien-11-olide; (4E,8E,12E,14E)-7-acetoxy-3,6,17,21-tetrahydroxy-6,10,12,16,20-pentamethyl-18,19-epoxytricosa-4,8,12,14-tetraen-11-olide; (8E,12E,14E)-7-acetoxy-3,6,17-trihydroxy-6,10,12,16-tetramethyl-18,19-epoxyheneicosa-8,12,14-trien-11-olide; (8E,12E,14E)-7-acetoxy-3,5,6,21,22-pentahydroxy-6,10,12,16,20-pentamethyl-18,19-epoxytricosa-8,12,14-trien-11-olide; (8E,12E,14E)-7-acetoxy-3,6,16-trihydroxy-6,10,

12,16-tetramethyl-18,19-epoxyheneicosa-8,12,14-trien-11-olide; (8E,12E,14E)-3,6,7,21-tetrahydroxy-6,10,16,20-tetramethyl-18,19-epoxytricosa-8,12,14-trien-11-olide; (8E,12E,14E)-7-acetoxy-3,6,17,21-tetrahydroxy-6,10,12,16,20-pentamethyl-18,19-epoxytricosa-8,12,14-trien-11-olide; (8E,12E,14E)-7-acetoxy-3,6,17-trihydroxy-6,10,12,16,18-pentamethyl-18,19-epoxyheneicosa-8,12,14-trien-11-olide; (8E,12E,14E)-7-acetoxy-3,6,21-trihydroxy-6,10,12,16,20-pentamethyl-5-oxo-18,19-epoxytricosa-8,12,14-trien-11-olide; and (8E,12E,14E,18E)-7-acetoxy-3,6,21-trihydroxy-6,10,12,16,20-pentamethyltricosa-8,12,14,18-tetraen-11-olide, said method comprising the steps of:

providing cyclodextrin in a culture broth of actinomycetes having an ability of producing the macrolide compound, culturing said actinomycetes in said culture broth to produce the macrolide compound, and separating the macrolide compound from said culture broth.

2. The method according to claim 1, wherein the macrolide compound is (8E,12E,14E)-7-acetoxy-3,6,21-trihydroxy-6,10,12,16,20-pentamethyl-18,19-epoxytricosa-8,12,14-trien-11-olide.

3. The method according to claim 1 or 2, wherein the cyclodextrin is one selected from the group consisting of β-cyclodextrin, γ-cyclodextrin, partially methylated β-cyclodextrin, dimethyl-β-cyclodextrin, glycosyl-β-cyclodextrin and hydroxypropyl-1-β-cyclodextrin.

4. The method according to claim 1, wherein the cyclodextrin is β-cyclodextrin.

5. The method according to claim 1, wherein the cyclodextrin is γ-cyclodextrin.

6. The method according to claim 1, wherein the cyclodextrin is partially methylated β-cyclodextrin.

7. The method according to claim 1, wherein the cyclodextrin is dimethyl-β-cyclodextrin.

8. The method according to claim 1, wherein the cyclodextrin is glycosyl-β-cyclodextrin.

9. The method according to claim 1, wherein the cyclodextrin is hydroxypropyl-β-cyclodextrin.

10. The method according to claim 1, wherein the concentration of the cyclodextrin in the culture broth is from 0.1 to 100 mg/mL.

11. The method according to claim 1, wherein the concentration of the cyclodextrin in the culture broth is from 10 to 30 mg/mL.

* * * * *

UNITED STATES PATENT AND TRADEMARK OFFICE
CERTIFICATE OF CORRECTION

PATENT NO. : 7,655,442 B2  Page 1 of 1
APPLICATION NO. : 10/587042
DATED : February 2, 2010
INVENTOR(S) : Ishihara et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 727 days.

Signed and Sealed this

Twenty-third Day of November, 2010

David J. Kappos
*Director of the United States Patent and Trademark Office*